United States Patent [19]

Schmidt et al.

[11] Patent Number: 4,620,049

[45] Date of Patent: Oct. 28, 1986

[54] METHOD AND APPARATUS FOR CONTROLLING POLYBUTENE PRODUCTION

[75] Inventors: Gregory E. Schmidt; Linus K. Leung, both of Naperville; Lawrence J. Beck, Bolingbrook, all of Ill.; David S. Chang, Cincinnati, Ohio

[73] Assignee: Standard Oil Company (Indiana), Chicago, Ill.

[21] Appl. No.: 666,896

[22] Filed: Oct. 31, 1984

[51] Int. Cl.$^4$ .............................................. C07C 2/00
[52] U.S. Cl. ...................................... 585/501; 526/60; 526/61; 585/701; 585/532; 422/131; 422/138; 208/DIG. 1
[58] Field of Search ................. 422/62, 119, 131, 138; 526/60, 61, 59; 585/501, 701, 532; 208/DIG. 1

[56] References Cited

U.S. PATENT DOCUMENTS

| 2,908,734 | 10/1959 | Cottle .................................... | 585/501 |
| 2,974,017 | 3/1961 | Morgan ................................ | 585/501 |
| 3,078,265 | 2/1963 | Berger et al. ........................ | 585/501 |
| 3,321,280 | 5/1967 | Trotter, Jr. et al. .................. | 422/62 |

OTHER PUBLICATIONS

Hall et al., in "Process Instruments and Controls Handbook", Ed., Considine, McGraw-Hill(1974), pp. 18–14 to 18–19.

*Primary Examiner*—William R. Dixon, Jr.
*Assistant Examiner*—A. Pal
*Attorney, Agent, or Firm*—William H. Magidson; William T. McClain; Ralph C. Medhurst

[57] ABSTRACT

The method is particularly adapted for controlling the molecular weight of a product output from a polybutene reactor. The method includes the steps of: deriving from the operating parameter of a polybutene reactor system a formula which correlates molecular weight as determined by product viscosity or other parameters of the product output with operating variables such as temperature of the reactor and concentration of isobutylene in the reactor, which concentration can be controlled by the amount of catalyst, e.g., aluminum chloride, being fed into the reactor; monitoring (a) the temperature of the reactor, (b) the concentration of isobutylene in the reactor, (c) the flow of coolant supplied to the reactor for controlling the temperature thereof and (d) the feed rate of catalyst into the reactor; calculating with said algorithm the approximate molecular weight of the product output; determining if the desired product molecular weight is higher or lower than the calculated molecular weight; and, if higher or lower, altering, through use of the formula, the temperature and/or the concentration of isobutylene in the reactor to obtain the desired product molecular weight.

Also the method can include the step of adding moisture to the feed or the reactor for lowering the molecular weight of the polybutene product output.

The apparatus includes a reactor, a computer and various sensing, monitoring and control devices for carrying out the steps of the method.

11 Claims, 5 Drawing Figures

METHOD AND APPARATUS FOR CONTROLLING POLYBUTENE PRODUCTION

BACKGROUND OF THE INVENTION

1. Field of the Invention

The present invention relates to the production of viscous polybutenes and more particularly relates to a method and apparatus for controlling the molecular weight of the polymeric butene product output from a polybutene reactor.

2. Description of the Prior Art

The manufacture of viscous polybutenes using a Friedel-Crafts catalyst system fed by a mixed butene monomer stream has been known for a long time. Various methods and apparatus using a Friedel-Crafts catalyst system for producing polybutenes are disclosed in the following U.S. Patents:

| U.S. Pat. No. | Patentee |
| --- | --- |
| 2,320,256 | Bailey, et al. |
| 2,469,725 | Heinrich |
| 2,657,246 | Schneider, et al. |
| 2,673,957 | Fontana, et al. |
| 2,957,930 | Jackson |
| 3,119,884 | Allen, et al. |
| 3,501,551 | Heidler, et al. |
| 4,306,105 | Abernathy et al. |
| 4,400,493 | Abernathy, Jr, et al. |
| 4,420,008 | Shu |

Heretofore it has been known that normally olefins containing approximately 4 carbons per molecule can be converted to viscous liquid polymers using Freidel-Crafts catalyst or Lewis acid catalyst, a preferred catalyst being aluminum chloride.

The typical olefin feed stock is a refinery stream from a cracking tower containing mixed butenes and butane, commonly referred to as a "B—B stream".

By controlling the parameters of operation of a polybutene reactor system including a polybutene reactor, a range of viscous polymer products can be obtained typically having molecular weights from approximately 900 up to approximately 5000.

The parameters that are controlled are the temperature of the reactor and the catalyst concentration in the reactor.

Although general correlations are known between the final molecular weight of the product output and the various controlled parameters such as temperature and catalyst concentration, it has heretofore been difficult to make adjustments to these parameters without knowing the actual molecular weight of the product as it is produced in order to obtain a desired molecular weight of the product output.

Since conventional laboratory techniques for the determination of molecular weight involve a relatively long procedure, such laboratory determination has been unsuitable for use in a polybutene reactor system for controlling input variables. Thus, it is desirable to provide some means, e.g., a method and/or an apparatus, for effecting immediate changes of controlled variables in response to the molecular weight of product as it is being produced. Such a method by which the molecular weight of the viscous polyolefin (polybutene) product output can be determined as it is being produced is very desirable since the information about the molecular weight of the product output could be used to immediately adjust controlled parameters of the polybutene reactor system.

As will be described in greater detail hereinafter, the method and apparatus of the present invention differ from the previously proposed methods and apparatus by providing a method and apparatus for monitoring certain concentrations of specific olefins in the feed stream and/or the reactor as well as the temperature of the reactor and including an empirically determined model by which the molecular weight of the polybutene product output can be predicted. Based upon a predicted or mathematically calculated molecular weight, a control circuit for the polybutene production system can determine what parameters should be altered or adjusted to produce a polybutene product output having a desired precise molecular weight.

SUMMARY OF THE INVENTION

According to the invention there is provided a method for controlling molecular weight of a viscous polybutene product from polymerization of a butene-containing feed using a Friedel-Crafts catalyst in a reactor comprising: (a) determining the isobutylene concentration and temperature in the reactor; (b) calculating a predicted molecular weight of the viscous polybutene product by the formula:

$$A0 - A1 \times T + A2 \times T^2 - A3 \times T \times (isoB) + A4 \times (isoB) - A5 \times (isoB^2)$$

wherein: MW is the weight average of molecular weight of polybutene product; T is the reactor temperature; (isoB) is the isobutylene concentration in the reactor; and A0–A5 are empirically determined coefficients; and (c) varying the temperature of catalyst concentration in the reactor whereby the molecular weight of the viscous polybutene product is changed is to a desired value.

Also, according to the invention there is provided a method for controlling the molecular weight of a product output from a polybutene reactor comprising the steps of: deriving from the operating parameters of a polybutene reactor system a formula which correlates molecular weight as determined by product viscosity or other parameter of the product output with operating variables such as temperature of the reactor and concentration of isobutylene in the reactor, which concentration can be controlled by the amount of catalyst, e.g., aluminum chloride, being fed into the reactor; monitoring (a) the temperature of the reactor, (b) the concentration of isobutylene in the reactor, (c) the flow of coolant supplied to the reactor for controlling the temperature thereof and (d) the feed rate of catalyst into the reactor; calculating with said algorithm the approximate molecular weight of the product output; determining if the desired product molecular weight is higher or lower than the calculated molecular weight; and, if higher or lower, altering, through use of the formula, the temperature and/or the concentration of isobutylene in the reactor to obtain the desired product molecular weight.

Further according to the invention there is provided an apparatus for controlling the molecular weight of a product output from a polybutene reactor comprising: a polybutene reactor, a control circuit coupled to the reactor; an algorithm based on a formula which is (a) derived from the operating parameters of a polybutene reactor system which correlates molecular weight as determined by product viscosity or other parameters of the product output with operating variables such as temperature of the reactor and concentration of isobutylene in the reactor, which concentration can be controlled by the amount of catalyst, e.g., aluminum chloride, being fed into the reactor and which is (b) stored in the control circuit; means coupled to the reactor and to the control circuit for sensing and monitoring the temperature of the reactor; means coupled to the reactor and to the control circuit for sensing and monitoring the concentration of isobutylene in the reactor; means coupled to the control circuit for monitoring the flow of coolant supplied to the reactor for controlling the temperature thereof; means coupled to the control circuit for monitoring the feed rate of catalyst into the reactor; means in the control circuit for calculating with the algorithm the approximate molecular weight of the product output and for determining if the desired product molecular weight is higher or lower than the calculated molecular weight; means responsive to calculated values of molecular weight for altering, through use of the formula, the temperature and/or the concentration of isobutylene in the reactor to obtain the desired product molecular weight.

Still further according to the invention, there is provided a method for controlling the molecular weight of the product output from a polybutene reactor where operating variables or parameters such as reactor temperature and isobutylene concentration in the reactor effluent can be controlled, the improvement comprising the step of injecting moisture into the reactor or into the butane-butene feed being fed into the reactor to reduce the molecular weight of the polybutene product output.

Additionally according to the invention, there is provided an apparatus for controlling the molecular weight of the product output from a polybutene reactor system including a polybutene reactor, means for controlling reactor temperature, means for controlling the concentration of isobutylene in the reactor effluent, and means for injecting moisture into the reactor or into the butane-butene feed being fed into the reactor to reduce the molecular weight of the polybutene product output.

DESCRIPTION OF THE PREFERRED EMBODIMENTS

Figure 1:
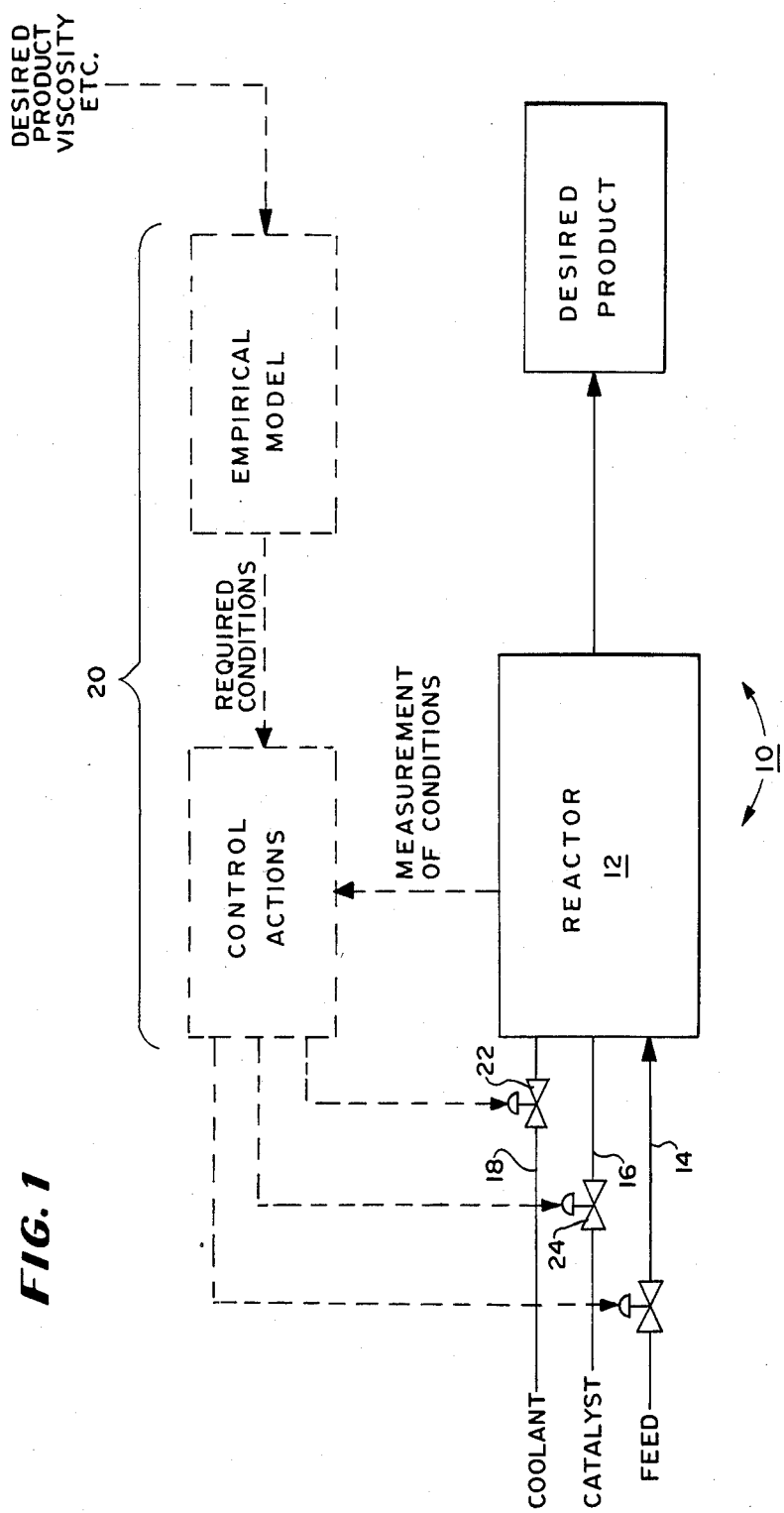
FIG. 1 is a block diagram of the apparatus of the present invention for selectively controlling polybutene production.

Referring now to the drawings in greater detail, there is illustrated in FIG. 1 a polybutene reactor system 10 constructed according to the teachings of the present invention. The polybutene reactor system 10 includes a reactor 12 in which an exothermic reaction takes place as a result of the feeding of a B—B stream via a feed input line 14, into the reactor 12. A catalyst is fed into the reactor 12 via a catalyst input line 16. In view of the exothermic heat generated within the reactor 12, a refrigerant or coolant is supplied via a coolant input line 18 to a jacket (not shown) situated around the reactor 12.

As is known in the art, a feed or stream of olefins are supplied to the reactor system from a cracking tower for cracking a particular type of crude oil. This feed or stream will react with a catalyst, such as aluminum chloride, in the reactor to create in the reactor a viscous liquid polymer.

According to the teachings of the present invention, the concentration of butenes in the reactor 12 are measured such as with a gas chromatography analyzer.

Another operating parameter of the reactor, of course, is the temperature, which can also be monitored by a thermocouple and altered as desired by altering the flow of coolant to the reactor 12 through a coolant input line 18.

The polybutene reactor system 10 of the present invention includes a control circuit 20 which can be realized by a microprocessor or computer with a memory including a ROM and a RAM. In the ROM is stored an empirical model of the reaction taking place within the reactor 12. A desired product viscosity or product molecular weight is supplied to the computer. This value of molecular weight is stored in the RAM and the empirical model is stored in the ROM of the memory.

The required conditions to obtain a desired molecular weight are calculated by the computer which then alters the flow of coolant supplied to the reactor 12 by operating a valve 22 in the coolant input line 18 and/or the amount of catalyst, aluminum chloride, in the reactor 12 by operating a valve 24 in the catalyst input line 16.

According to the method of the present invention, the molecular weight of the desired product output of a viscous polybutene is controlled by measuring and monitoring the concentration of isobutylene in the reactor 12. Then, this value of isobutylene concentration in the reactor 12 is plugged into a formula of the empirical model stored in the ROM relating isobutylene concentration in the reactor 12 to product molecular weight. Then a predicted molecular weight of the viscous polybutene product output is calculated and if this molecular weight varies from a desired target molecular weight the variables of reactor temperature or feed of catalyst to the reactor 12 are adjusted by the computer in the control circuit 20. It is to be noted here that the amount of catalyst supplied to the reactor 12 determines to a great extent the amount of isobutylene concentration in the reactor 12.

The mathematical formula is determined by making a number of measurements of molecular weight of the product output for different temperatures of the reactor 12 and for different concentrations of the isobutylene concentration in the reactor 12 correlated with the feed of catalyst to the reactor 12.

The viscous olefin polymer (polybutene) produced by the reactor system 10 is produced by polymerizing $C_4$ olefins over a catalyst. A typical $C_4$ olefin monomer feedstream contains mixed butenes, i.e., butene-1, cis-2-butene, trans-2-butene, and isobutylene, saturated hydrocarbons, i.e. normal butane and isobutane and can contain minor amounts of $C_3$ and $C_5$ hydrocarbons. These $C_4$ olefins in the feed typically come from refinery operations such as from a cracking tower, i.e., a tower for steam cracking or catalytic cracking. In the polybutene reactor system 10 of the present invention, the C₄ olefin stream is contacted with a catalyst, such as aluminum chloride, in the reactor 12 and the polymeric product of polybutene is removed and separated from unreacted monomer. A polybutene production system of this type is described in U.S. Pat. No. 3,501,551. Such polymerization reaction can be carried out at temperatures ranging from −40° to 120° F. and typically the polymerization temperatures range from 0° F. to 100° F.

Figure 2:
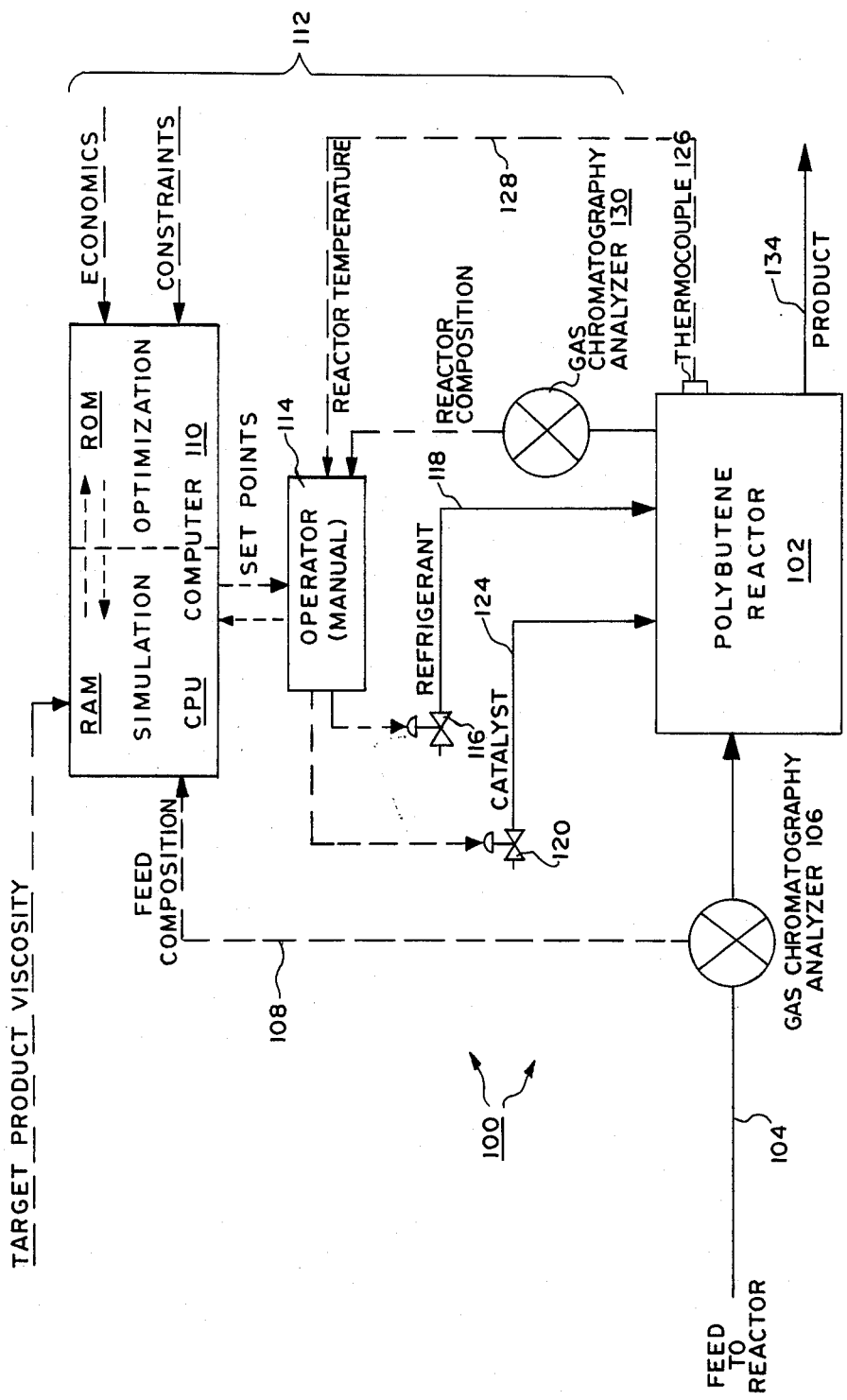
FIG. 2 is a block diagram of another embodiment of the apparatus of the present invention for selectively controlling polybutene production.

A more detailed realization of the method and apparatus of the present invention is shown in FIG. 2. Here a polybutene reactor system 100 includes a polybutene reactor 102 which is supplied with a B—B stream via an feed inlet line 104. This feed or stream input is monitored by a gas chromatography analyzer 106 which is coupled to the feed input line 104. The feed composition, as determined by the gas chromatography analyzer 106, is supplied via an electrical circuit 108 to a computer 110. At the same time a target product viscosity, related to molecular weight, is supplied to the computer 110.

The computer 110 is part of a control system 112 which can be partially manual and partially automatic and once initial operating set points are established manually, the computer 110 can operate the reactor system 100 automatically. In this respect, the control system 112 includes not only the computer 110 but also a control panel and keyboard 114 by which an operator can set the initial temperature, the initial amount of refrigerant coolant supplied through a valve 116 to a refrigerant input line 118 and the initial amount of catalyst, e.g., aluminum chloride, fed to the reactor 102 through a valve 120 and a catalyst input line 124. The temperature of the reactor is sensed and monitored by means of a thermocouple 126 coupled to the reactor 102 and a temperature signal is supplied via an electrical circuit 128 to the operator panel 114.

The reactor composition is analyzed by another gas chromatography analyzer 130 which determines the concentration of various components in the reactor, particularly isobutylene, and supplies such information to the operator panel 114, which information is then supplied to the computer 110. With this information, the computer 110, utilizing an empirically determined model based upon a formula relating molecular weight of the polybutene product in an output line 134 with the primary variables of reactor temperature and the concentration of isobutylene in the reactor 102, can predict the molecular weight of polybutene product output.

In the use of the polybutene reactor system 100 illustrated in FIG. 2, the selective polymerization of isobutylene from its admixture with other low-boiling olefins is controlled under such conditions as will result in production of polymers of high reactivity of normal ranges of molecular weight.

It is well known that olefins in a C₄ cut can be polymerized with solid aluminum chloride catalyst to provide polymers having Saybolt viscosities of between 40 and 20,000 at approximately 210° F. In a typical polymerization process, isobutylene and other hydrocarbons of 3 to 5 carbons per molecule are contacted with the powdered aluminum halide at a temperature from approximately −40° F. to approximately 120° F. and a pressure sufficient to prevent any substantial amount of vapor phase in the polymerization reactor 102.

In this complicated process, there are many process variables that will affect the operation of the system 100. Some of these variables are controllable, but most of them are not. Since the effects of many of the process variables are interactive, it has not heretofore been considered possible to determine a particularly effective method to evaluate the outcome brought about by changing one or more variables via an empirical simulation or model of the process.

According to the teachings of the present invention, an empirical model or simulation has been found to be effective in evaluating the outcome brought about by changing one or more variables. In this respect, an equation was derived from experimental data weight of a produced polymer product i.e. a polybutene product and was found to be accurate in describing the molecular output, as a function of reaction temperature, concentration of monomers in the reactor 102 and their reaction. This empirical equation is applicable to all different feed stocks and can be a very useful tool at any plant to predict product grade immediately from reaction conditions.

It was further found that residence time had little effect on product viscosity.

Also, for a given feed stock and a determined product viscosity range, product yield can be increased by operating at a lower temperature and a higher isobutylene conversion in the reactor.

Still further, product yield was found to also be greatly increased by using a feed stock having as high as possible isobutylene concentration and as low as possible cis-2-butene concentration.

Utilizing this empirically determined equation, an empirical model can be mathematically constructed and stored in a ROM of a computer for providing a controlled process for selective polymerization of isobutylene.

The basic equation that was empirically determined is as follows:

$$MW = A0 - A1 \times T + A2 \times T^2 - A3 \times T \times (isoB) + A4 \times (isoB) - A5 \times (isoB)^2$$

where:

MW is the weight averaged molecular weight of the polybutene product output;

T is the reaction temperature, i.e. the measured temperature of the reactor;

(isoB) is the isobutylene concentration in the reactor; and

A0 to A5 are empirically determined coefficients.

The ranges of the variables or parameters and the coefficients are as follows:

| | Range: | | |
|---|---|---|---|
| MW | from | 300 | to | 10000 |
| T | from | 0 | to | 100° F. |
| (isoB) | from | 0.8 | to | 15 wt % |
| A0 | from | 1900 | to | 2900 |
| A1 | from | 40 | to | 83 |
| A2 | from | 0.20 | to | 0.70 |
| A3 | from | 7.8 | to | 12 |
| A4 | from | 820 | to | 1200 |
| A5 | from | −1.6 | to | 23 |

The above equation and the coefficients for the range of variables/parameters indicated above, namely the different values of temperature and isobutylene concentration, were determined by conducting a sufficient number of experiments in which polybutene products were made with different reactor temperatures and different isobutylene concentrations. The molecular weights of the resulting product were correlated with the reactor temperature and isobutylene concentration using non-linear regression techniques to determine the coefficients A0–A5 in the equation.

Further study and experiments indicated that other correction factors or refinements to the equation set forth above can be added to the equation to more accurately determine or predict molecular weight of the polybutene product output. These correction factors were determined for:

1. cis-2-butene;
2. moisture present in the feed;
3. 1,3-butadiene; and
4. 1,2-butadiene.

These correction factors are identified as CORR1, CORR2, CORR3 and CORR4 and are explained in detail below:

1. Cis-2-butene:

$$\text{CORR1} = -B0 \times (c\text{-}2\text{-}B) \times (T - B1) \quad \text{if } T \geq B1$$
$$= 0 \quad \text{if } T < B1$$

where:

CORR1 is the correction to MW which is due to the cis-2-butene concentration in the reactor and which is to be added to the basic equation for MW set forth above;

(c-2-B) is the cis-2-butene concentration in the reactor 102;

T is the reaction temperature; and

B0 and B1 are empirically determined coefficients.

| | Range: | | | |
|---|---|---|---|---|
| (c-2-B) | from | 0 | to | 15 wt % |
| T | from | 0 | to | 100° F. |
| B0 | from | 0.54 | to | 0.85 |
| B1 | from | 10 | to | 30 |

The empirically determined coefficients B0 and B1 were determined by making sufficient experiments in which polybutene products were made with different reactor temperatures, different isobutylene concentrations and different cis-2-butene concentrations. Then the deviation of the molecular weights of the resulting products and those calculated with the basic equation were correlated with the reactor temperature and the cis-2-butene concentration using linear regression techniques to empirically determine the coefficients B0 and B1.

2. Moisture:

$$\text{CORR2} = -C0 \times (H_2O)$$

where:

CORR2 is the correction to MW due to moisture in the feed and which is to be added to the basic equation;

($H_2O$) is the moisture content in the feed; and C0 is an empirically determined coefficient.

| | Range: | | | |
|---|---|---|---|---|
| ($H_2O$) | from | 0 | to | 100 ppmw |
| C0 | from | 2.7 | to | 16 |

The coefficient C0 was determined by conducting sufficient experiments in which polybutene products were made with different reactor temperatures, different isobutylene concentrations and different moisture levels. Then the deviation of the molecular weights of the resulting products and those calculated with the basic equation were correlated with the moisture level using linear regression techniques to empirically determine the coefficient C0.

3. 1,3-butadiene:

$$\text{CORR3} = D0 \times (1,3\text{-BD}) \times (T - D1) \quad \text{if } T > -D1$$
$$0 \quad \text{if } T < D1$$

where:

CORR3 is the correction to MW which is due to 1,3-butadiene and which is to be added to the basic equation;

(1,3-BD) is the 1,3-butadiene concentration in the feed;

T is the reaction temperature; and D0 and D1 are empirically determined coefficients.

| | Range: | | | |
|---|---|---|---|---|
| (1,3-BD) | from | 0 | to | 1 wt % |
| T | from | 0 | to | 100° F. |
| D0 | from | 7.7 | to | 26 |
| D1 | from | 10 | to | 30 |

The coefficients D0 and D1 were determined by conducting sufficient experiments in which polybutene products were made with different reactor temperatures, different isobutylene concentrations, and different 1,3-butadiene concentrations. Then the deviation of the molecular weights of the resulting products and those calculated with the basic equation were correlated with the reactor temperature and the 1,3-butadiene concentration using linear regression techniques to empirically determine the coefficients D0 and D1.

4. 1,2-butadiene:

$$\text{CORR4} = f(1,2\text{-BD})$$

where:

CORR4 is the correction to MW due to the concentration of 1,2-butadiene. This CORR4 is to be added to the basic equation set forth above;

(1,2-BD) is the concentration of 1,2-butadiene in the feed; and f is a functional notation.

CORR4 will increase with increasing (1,2-BD).

| | Range: | | | |
|---|---|---|---|---|
| (1,2-BD) | from | 0 | to | 1000 ppmw |

Figure 3:
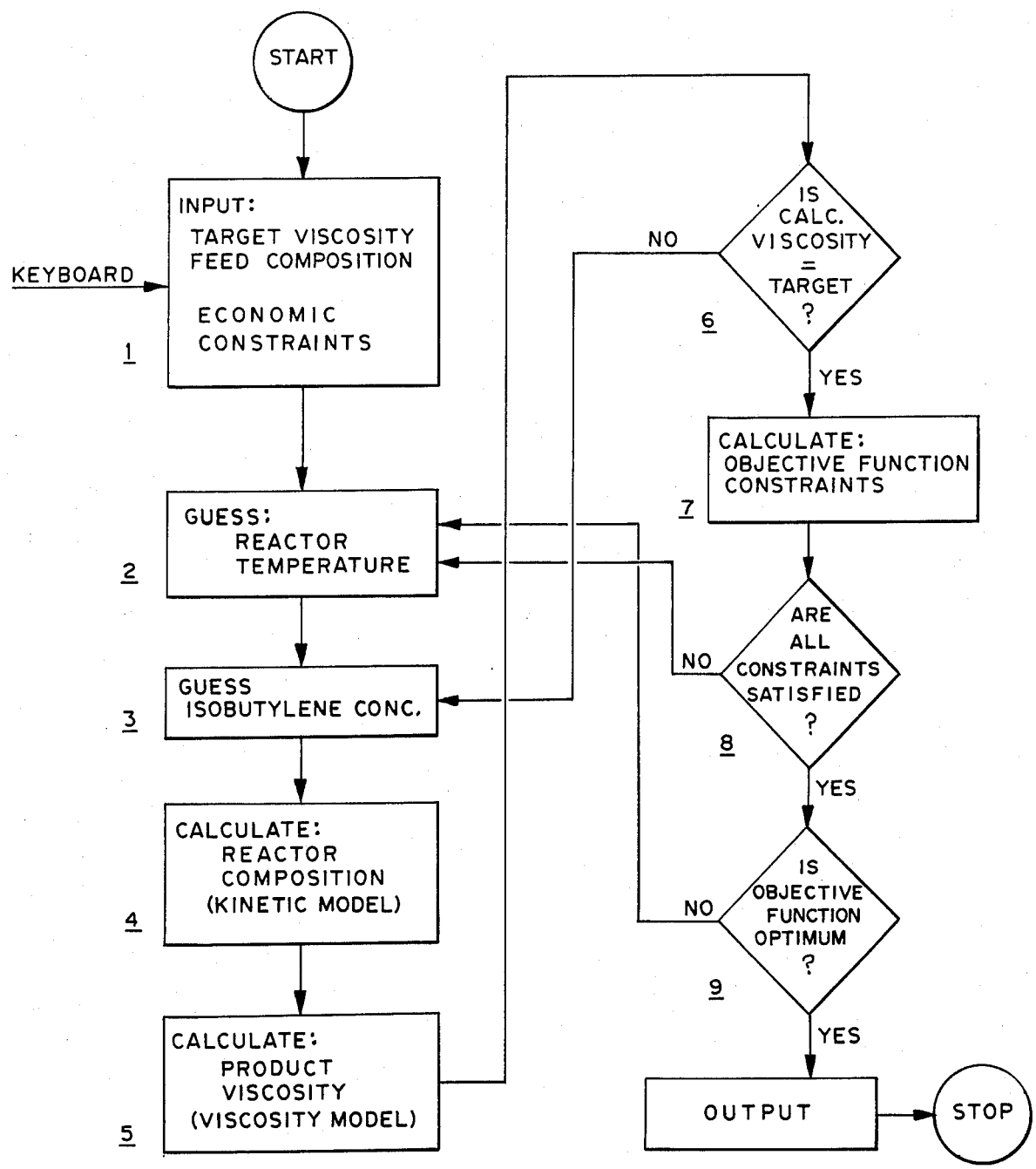
FIG. 3 is a flow chart of the program carried out by the computer of the appratus shown in FIG. 2 for controlling polybutene production.

Referring now to FIG. 3, there is illustrated therein a flow chart of a program protocol or routine carried out in and by the computer 110 in controlling the polymer product output from the reactor 102. The routine includes the following steps:

STEP 1. As shown, the polybutene production system 100 is first started up and then at the first step an operator will plug in various inputs such as target viscosity, the feed composition, and economic factors and operation constraints.

With respect to economic factors, there are other variables which can be altered to change variables of the polybutene production in the reactor 102. In this respect, if one wanted to adjust the amount of isobutylene in the feed, one can adjust the temperature of cracking in the cracking tower. This is an alternative to supplying more catalyst, such as aluminum chloride, to the reactor 102. However, at present, the economic cost for changing the operating temperatures in the cracking tower is much greater than the cost in changing the amount of aluminum chloride catalyst fed into the reactor 102. Thus, the computer typically will be programmed not to change the cracking tower temperature.

However, conditions may exist where, to obtain a desired molecular weight of the polybutene product output, it is desirable to change the cracking tower temperature to increase the isobutylene in the feed. It is understood that these conditions will be included in the empirical model stored in the ROM.

STEP 2. At step 2, a first reactor temperature is estimated by the computer 110, sensed by the thermocouple 126 or input manually by the operator.

STEP 3. Here the isobutylene concentration is estimated by the computer 110, determined by the analyzer 130 or punched in the keyboard 114 by the operator.

STEP 4. Here the computer calculates, using the basic equation in the empirical model, the composition of the components in the reactor.

STEP 5. Here the computer 110 calculates the product viscosity from the empirical model.

STEP 6. Here the computer 110 determines whether the calculated viscosity for the temperature and isobutylene concentrations plugged into the empirical model will provide the desired target viscosity. If NO, the computer 110 then cycles back to step 3 to make another estimation of isobutylene concentration and loops back through STEPS 4, 5 and 6.

STEP 7. When the calculated viscosity equals approximately the target viscosity, the computer 110 goes on to step 7 where an objective function such as operating cost, and operation constraints such as refrigeration compressor load are calculated.

STEP 8. At step 8, the computer determines whether all the constraints are satisfied. If not, it loops back to STEP 2 to estimate a new reactor temperature.

STEP 9. At step 9, the computer determines whether the objective function is optimal. If NO, the program loops back to STEP 2 to again adjust reactor temperature. If YES, the output is predicted to have, or determined to have, the target viscosity. Here the computer 110 then exits the routine. Typically, in the implementation of the formula and the algorithm incorporating same, namely in carrying out the method of the present invention and/or operating the apparatus of the present invention when the calculated molecular weight of the polybutene product is higher than the desired molecular weight of the polybutene product, the first step would be to increase temperature. The second step would be to increase the amount of catalyst supplied to the reactor to increase the amount of isobutylene being formed in the reactor. Alternatively, one could change the temperature of a fractionating tower to change the isobutylene concentration in the reactor. At present this cost is prohibitive.

A third step would be to add water as will be described in greater detail hereinbelow to reduce the molecular weight.

When the calculated molecular weight of the polybutene product is less than the desired molecular weight of the desired polybutene product, one would first reduce the temperature and secondly reduce the amount of catalyst being supplied to the reactor thereby to increase the molecular weight of the polybutene product output.

Figure 4:
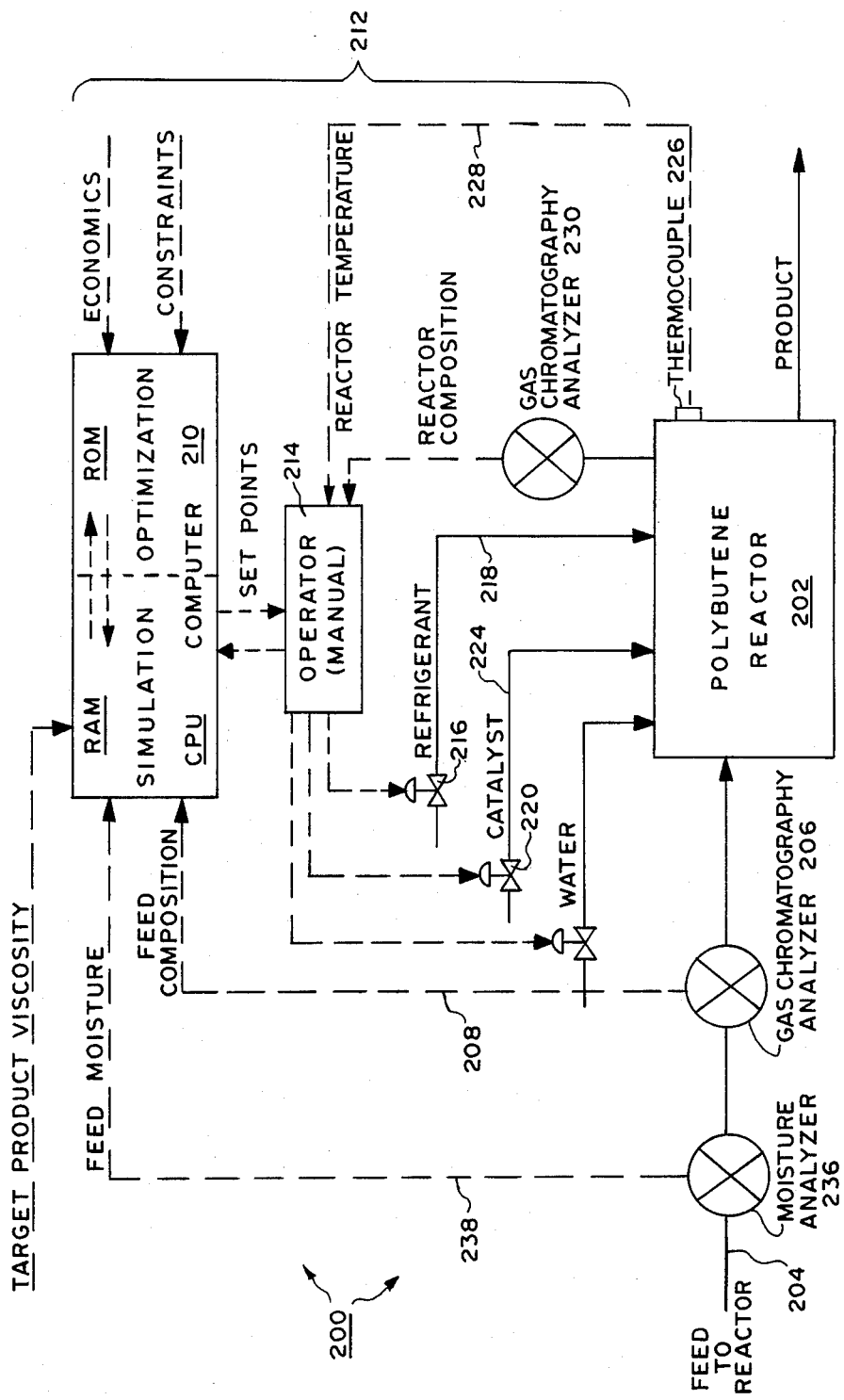
FIG. 4 is a block diagram of another embodiment of the apparatus of the present invention for controlling polybutene production in which water is utilized in the control of polybutene production.

Referring now to FIG. 4, there is illustrated therein a polybutene reactor system 200 comprising many of the same components as the system 100 shown in FIG. 3. In this respect, the polybutene reactor system 200 includes a reactor 202, a feed input line 104, a gas chromatography analyzer 206, an electrical circuit 208, a computer 210 with a RAM, a ROM and a CPU forming part of a control circuit 212, and a keyboard operator panel 214. The panel 214 is coupled to the computer 210 for receiving set points from the computer 210 or manually from the operator and for supplying the computer 210 with data on the temperature of the reactor 202 and the composition of the various products being formed in the reactor 202 as well as information on the refrigerant being supplied to the reactor 202 and the catalyst being supplied to the reactor 202.

For this purpose the system 200 further includes a refrigerant valve 216, a refrigerant input line 218, a catalyst valve 220, a catalyst input line 224, a thermocouple 226, an electric circuit 228, a gas chromatography analyzer 230 and a product output line 234 substantially identical to similarly numbered components in FIG. 2.

Target product viscosity is also supplied to the computer 210.

Further, economic factors and operation constraints are supplied to the computer 210 either by being included in the empirical model or by being supplied thereto from the keyboard 114.

However, additionally, a moisture analyzer 236 is provided in the input feed line 204 for determining the amount of moisture in the feed. This feed moisture value is fed to the computer 210 via an electric circuit 238 so that a correction factor, CORR2, based on feed moisture can be added to the basic equation described above.

Further, in this system 200, moisture or water can be supplied to the polybutene reactor 202 to control the molecular weight of the polybutene product output.

In accordance with the teachings of the present invention, it has been discovered that the polybutene molecular weight and viscosity of the polybutene product output can be significantly reduced in a controlled fashion by the intentional addition of moisture or water to the butanes-butenes feed stock (B—B stream) supplied to the reactor 202.

For example, in the manufacture of low molecular weight polybutene having a molecular weight of approximately 650, under controlled conditions of reactor temperature and concentrations of cis-2-butene and isobutylene in the reactor effluent which are currently being used to prepare higher molecular weight polybutene having a molecular weight of approximately 920 from dry feeds, water can be added. In this way, an increase in the polybutene yield can be obtained due to more efficient use of normal butenes, particularly 1-butene and cis-2-butene in B—B streams. This method of preparing low molecular weight polybutene is especially beneficial in a feed or capacity-limited environment.

From numerous tests it has been determined that feed moisture exerts an effect upon the polybutene molecular weight and viscosity independently of the other process variables involved in butene polymerization that are known to impact on polybutene molecular weight and viscosity. The other variables are, as described above, the temperature of the reactor, the concentration of isobutylene in the reactor effluent and the concentration of cis-2-butene in the reactor effluent. Tests have shown that addition of water or moisture significantly reduces the polybutene molecular weight and viscosity. This has been found to be true under a wide range of reaction conditions. Also, it has been found that the effect of feed moisture or water on polybutene molecular weight and viscosity is potentially greatest at high levels of isobutylene concentration in the reactor effluent.

In accordance with the teachings of the present invention, moisture or water is added either into the B—B stream feed to the reactor 202 or directly to the reactor 202 itself. In the illustrated embodiment, water is supplied through a valve 240 to a water input line 242 to the reactor 202. The valve 240 is controlled via an electric circuit 244 coupled between the valve 240 and the computer 210.

By adding moisture to the reactor 202, it is possible to prepare straight-runs of low molecular weight polybutene having molecular weights of approximately 300 and 320, respectively, with high selectivities. Without adding moisture, polybutene with such low molecular weight can only be obtained in small quantities via fractionation of the polybutene products of normal molecular weight, typically ranging from 900 to 5000. It also permits one to prepare polybutenes of a particular molecular weight and viscosity at lower reactor temperatures and/or at higher isobutylene concentrations in the reactor effluent than heretofore was possible. In this respect, low molecular weight polybutene can be manufactured under conditions that are currently used to prepare higher molecular weight polybutene from dry feeds. Also as noted above, by adding water or moisture to the feed or to the reactor one can make more efficient use of normal butenes.

Furthermore, addition of moisture or water can have beneficial effects on the other important polymer properties as well as on the amount of catalyst required to prepare polybutene products having a desired molecular weight.

Of the process variables of butene polymerization in the reactor 202 of the system 200 that affect polybutene molecular weight and viscosity, namely reactor temperature, concentration of isobutylene and concentration cis-2-butene in the reactor effluent, the reactor temperature and the isobutylene concentration are the easiest to control. Accordingly, to determine the effect of water on the molecular weight of the polybutene product produced various tests were made with water-promoted runs in which a typical refinery B—B stream feed was spiked with 60 to 100 ppmw and the feed was polymerized and the resulting products were compared to those obtained from control runs in which dry (less than 5 ppmw) feed of identical composition was used. Corresponding runs were conducted at the same reactor temperature ranging from 35° to 110° F. and isobutylene concentration ranging from 0.2 to 2.6 weight % so that the effect of these important variables on polybutene molecular weight and viscosity could be eliminated.

From the results of these test runs, it was noted that heavy polymer viscosity and molecular weight were significantly reduced in all the water-promoted runs relative to the "dry" runs. Also, the higher the level of isobutylene concentration in the reactor effluent, the lower the viscosity and molecular weight of the polybutene product output from the wet feed. For example, in one case the molecular weight (Mn by VPO) and viscosity of the polybutene prepared from the dry feed were 1037 and 312 cs, respectively. Then with the intentional addition of moisture to the feed the molecular weight and viscosity of the polymer dropped to 675 and 75 cs, respectively. This difference shows that significant changes in polymer properties can be achieved by the presence of water or moisture in the reactor feed.

According to the teachings of the present invention, water-promoted runs provide significant decreases in the polybutene molecular weight and viscosity independently of the other process variables of butene polymerization.

It has been determined that process variables can be controlled within certain ranges to obtain certain beneficial results in the control of the molecular weight of the polybutene product output from the reactor 202 of the polybutene reactor system 200. In particular, with reactor temperatures ranging from 35° to 110° F., isobutylene levels in the reactor effluent ranging from 0.2 to 2.6 weight % and moisture levels in the B—B stream feed ranging from 60 to 100 ppmw, one is able to determine or predict fairly accurately polybutene molecular weight of the product output. Also, again, feed moisture will have the greatest potential affect on polybutene molecular weight and viscosity when the isobutylene in the reactor effluent is high.

The amount of moisture added can be varied within a range of 5 to 500 ppmw to reduce the molecular weight of the polybutene product output to a value of under 2000 and in a range between 300 and 2000. Typically, the range will be between 300 and 1000 and the addition of moisture is very significant in the production of polybutenes in the range between 300 and 800 molecular weight.

The addition of moisture is very helpful in the manufacture of very low molecular weight polybutenes, as noted above, which are not currently accessible using conventional process conditions. For example, with the addition of moisture or water, it is possible to prepare straight runs of low molecular weight polybutenes with high selectivities. Also, with the addition of moisture and the control of the other variables, such as reaction temperature and isobutylene concentration, polybutenes of a particular molecular weight and viscosity at low reactor temperatures and/or high isobutylene concentrations in the reactor effluent can be obtained that were not heretofore obtainable. Also as noted above, addition of water permits the use of normal butenes in the reaction, particularly 1-butene and cis-2-butene.

Figure 5:
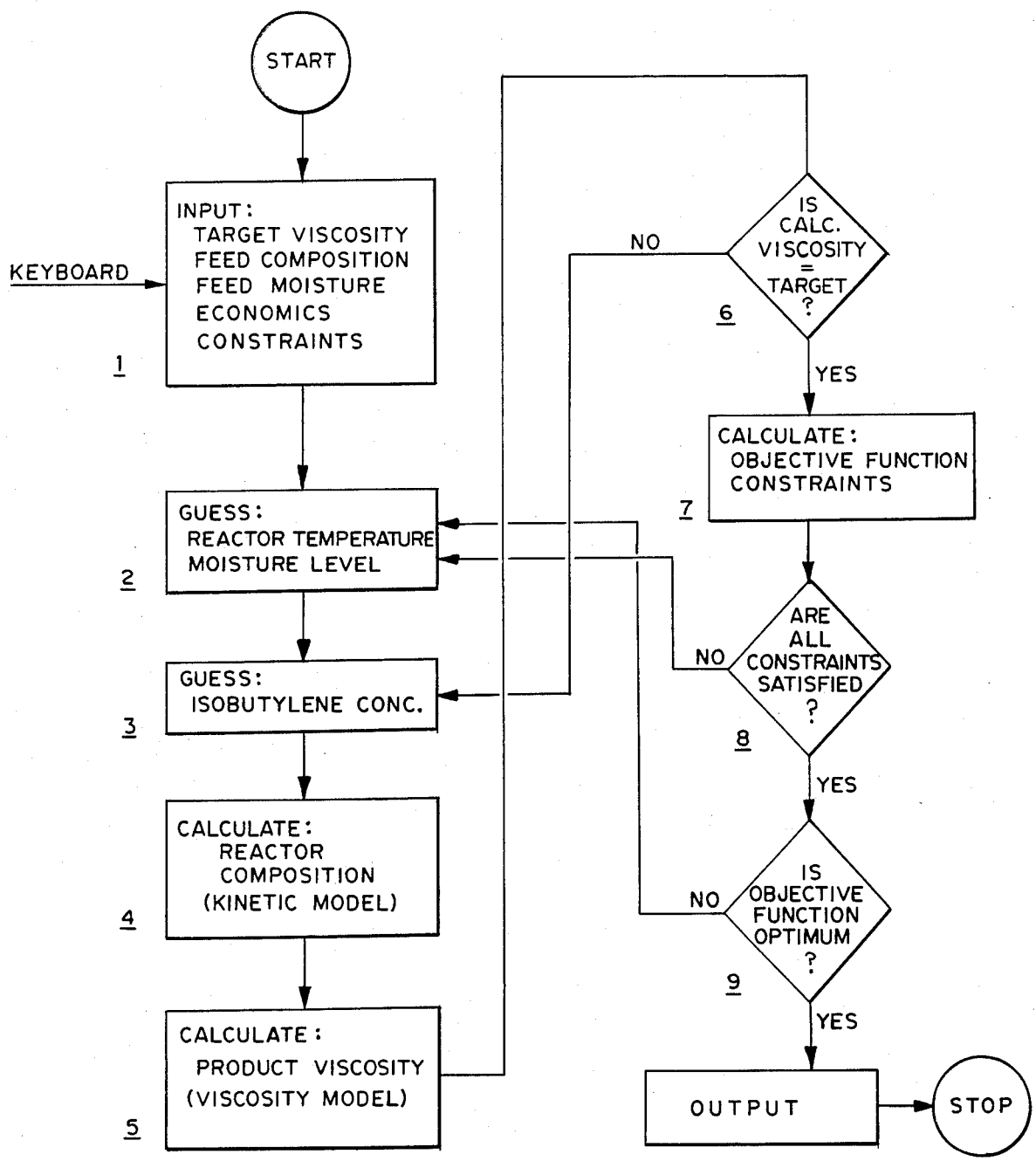
FIG. 5 is a flow chart of the program carried out by the computer in the apparatus of FIG. 4 in controlling polybutene production.

In FIG. 5 is set forth a flow chart of the protocol, program, or routine carried out by the computer 210 in the polybutene reactor system 200 shown in FIG. 4. Here the steps 1–9 are identical to the steps 1–9 in the flow chart shown in FIG. 3. However, step 1 includes an additional factor of feed moisture of the feed which factor is inputted into the computer 210 along with the other variables and constraints.

Furthermore, at step 2, an estimation is made not only of the desired reactor temperature but also the desired moisture level.

Then, at steps 8 and 9, if the constraints are not satisfied or the objective function is not at optimum, the moisture level as well as the reactor temperature can be adjusted to obtain the desired product output having a desired molecular weight and viscosity.

From the foregoing description, it will be apparent that the method and apparatus of the present invention for controlling selectively the molecular weight of a polybutene product output has a number of advantages some of which have been described above and others of which are inherent in the invention.

Also, it will be apparent that modifications can be made to the method and apparatus of the present invention without departing from the teachings of the invention. Accordingly, the scope of the invention is only to be limited as necessitated by the accompanying claims.

We claim:

1. A method for controlling the molecular weight of the product output from a polybutene reactor where operating variables in the reactor are controlled, said method comprising the step of injecting moisture into the reactor or into the butene-butene feed being fed into the reactor.

2. The method of claim 1 wherein said controlled operating variables in the reactor include the isobutylene concentration, and said isobutylene concentration is maintained at a high level.

3. The method of claim 1 wherein moisture is added in a range of approximately 5 to up to approximately 500 ppmw to reduce the molecular weight of the product output to under 2000.

4. The method of claim 3 wherein said molecular weight of the output product is reduced to a value under 1000.

5. The method of claim 3 wherein said molecular weight of the product output is reduced to a value of between 300 and 800.

6. The method of claim 1 wherein the reactor is maintained at a temperature between 0° and 110° F.

7. The method of claim 6 wherein the temperature of the reactor is maintained between 35° F. to 100° F.

8. An apparatus for controlling the molecular weight of the product output from a polybutene reactor system including a polybutene reactor, means for controlling reactor temperature, means for controlling the concentration of isobutylene in the reactor effluent, and means for injecting moisture into said reactor or into the butene-butene feed being fed into said reactor to reduce the molecular weight of the polybutene product output.

9. The apparatus of claim 8 including means for maintaining the isobutylene concentration in the reactor effluent at a high level.

10. The apparatus of claim 8 wherein said means for injecting moisture is operable to add water in a range of approximately 5 to up to approximately 500 ppmw to reduce the molecular weight of the product output to under 2000 and to as low as 300.

11. The apparatus of claim 8 wherein said reactor temperature control means is operable to control the temperature of the reactor between 0° and 110° F.

* * * * *